(12) United States Patent
Bae (10) Patent No.: US 8,365,578 B2
(45) Date of Patent: Feb. 5, 2013

(54) ROTARY PARTICLE SENSOR ASSEMBLY AND AN AIR CLEANER HAVING IT

(75) Inventor: Jun Hyung Bae, Seoul (KR)

(73) Assignee: Woongjin Coway Co., Ltd., Chungcheongnam-do (KR)

( * ) Notice: Subject to any disclaimer, the term of this patent is extended or adjusted under 35 U.S.C. 154(b) by 237 days.

(21) Appl. No.: 12/672,541

(22) PCT Filed: Aug. 7, 2008

(86) PCT No.: PCT/KR2008/004581
§ 371 (c)(1),
(2), (4) Date: Dec. 29, 2010

(87) PCT Pub. No.: WO2009/020355
PCT Pub. Date: Feb. 12, 2009

(65) Prior Publication Data
US 2011/0120211 A1 May 26, 2011

(30) Foreign Application Priority Data

Aug. 8, 2007 (KR) .................. 10-2007-0079679

(51) Int. Cl.
*G01N 1/00* (2006.01)
(52) U.S. Cl. .................................. 73/28.04
(58) Field of Classification Search ............. 73/28.04, 73/31.07, 31.02
See application file for complete search history.

(56) References Cited

U.S. PATENT DOCUMENTS

| 6,779,380 B1 * | 8/2004 | Nieuwkamp | 73/28.01 |
| 8,266,945 B2 * | 9/2012 | Hartshorne | 73/28.04 |
| 2010/0024522 A1 * | 2/2010 | Hartshorne | 73/28.04 |

FOREIGN PATENT DOCUMENTS

| JP | 5-164682 | 6/1993 |
| JP | 7-134094 | 5/1995 |
| JP | 2794049 | 9/1998 |
| KR | 20-363865 | 10/2004 |
| KR | 10-0871540 B1 | 11/2008 |
| WO | WO 2006/016345 A1 | 2/2006 |

OTHER PUBLICATIONS

International Search Report and Written Opinion for PCT International Application No. PCT/KR2008/004581 mailed Feb. 17, 2009.
Supplementary European Search Report for Application No. EP 08 79 3095 mailed Aug. 5, 2010.
Notice of Allowance for Korean Application No. 10-2008-0077147.

* cited by examiner

*Primary Examiner* — Jewel V Thompson
(74) *Attorney, Agent, or Firm* — RatnerPrestia (57) ABSTRACT

A rotary particle sensor assembly and an air cleaner having the rotary particle sensor assembly are disclosed. Particularly, in the present invention, regardless of the orientation of the air cleaner, the rotary particle sensor assembly can always be oriented in the direction of gravity. The rotary particle sensor assembly includes a particle sensor, which measures the pollution level of air drawn into the air cleaner. The particle sensor is supported in the air cleaner so as to be rotatable using a rotating shaft and has a weight at a predetermined position. Thus, the particle sensor can always be oriented in the direction of gravity by the weight regardless of the orientation of the air cleaner. Therefore, the present invention ensures the accuracy of measurement of the pollution level of air.

13 Claims, 6 Drawing Sheets

< vertical >

< horizontal >

ROTARY PARTICLE SENSOR ASSEMBLY AND AN AIR CLEANER HAVING IT

This application is a U.S. National Phase Application of PCT International Application No. PCT/KR2008/004581, filed Aug. 7, 2008.

FIELD OF THE INVENTION

The present invention relates, in general, to rotary particle sensor assemblies and air cleaners having the rotary particle sensor assemblies and, more particularly, to a rotary particle sensor assembly, which can always be oriented in a predetermined direction regardless of the orientation of an air cleaner, and the air cleaner having such a rotary particle sensor assembly.

BACKGROUND OF THE INVENTION

As is well known to those skilled in the art, particle sensors are devices, which measure the amount of and sizes of minute particles contained in air. The particle sensors are installed in various kinds of apparatuses, such as air conditioners, air cleaners, etc., which purify air or perform the operation of drawing air in and discharging it.

Such a particle sensor measures the amount and sizes of minute particles while an apparatus, such as an air cleaner having the particle sensor, is being operated, thus providing information about air pollution levels to the apparatus so that the apparatus can be effectively operated.

Figure 1:
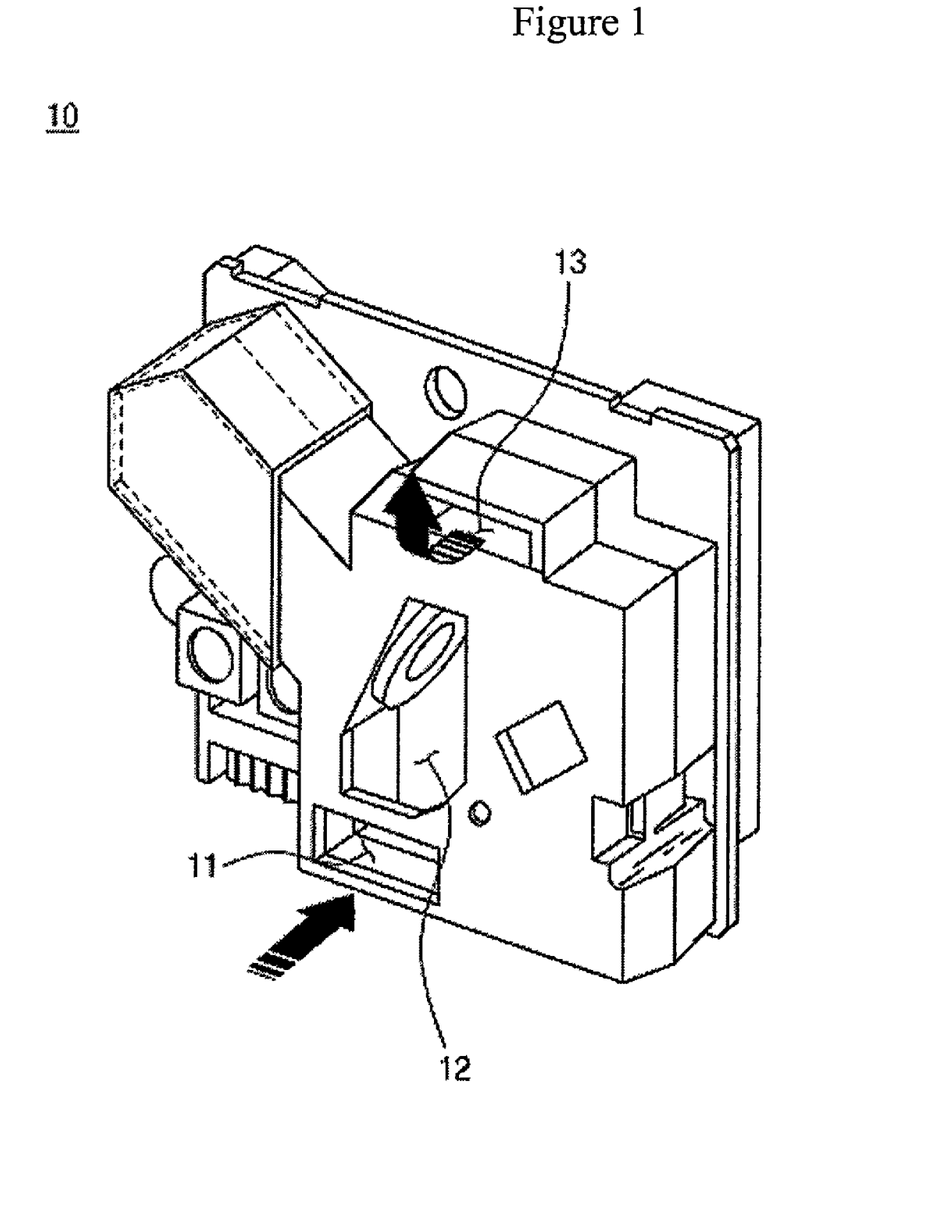
FIG. 1 is a perspective view of a conventional particle sensor.

Referring to FIG. 1, a typical particle sensor 10 has an inlet 11 into which air is drawn, a detection chamber 12 provided to measure pollution levels of the air, and an outlet 13 through which the air that has its pollution levels measured is discharged to outside the particle sensor.

Generally, the particle sensor 10 measures the pollution levels of air using a method of applying light to air flowing by natural convection and not by forced convection. In this case, to ensure the accuracy of measurement, air drawn into the inlet 11 must flow towards the outlet 13 through the detection chamber 12 in the direction opposite that of gravity, that is, upwards. The reason for this is that air flowing by natural convection is moved upwards from the lower position to the upper position owing to differing densities of the air.

Here, a difference in density of air is caused by expansion of air due to heat generated from a resistor, which is a typical electronic component and is provided around the inlet 11. In other words, air drawn into the apparatus, such as the air cleaner, is expanded by heat and is thus reduced in density. The air that is reduced in density becomes lighter, thus moving upwards.

As such, the resistor, which is a typical electronic component and is provided around the inlet 11, serves as a heat source, so that air drawn into the inlet 11 is expanded by heat generated from the resistor and is thus moved upwards. At this time, pollution levels of the air are measured in the detection chamber 12 and, thereafter, the air is continuously moved upwards and discharged through the outlet 13 to the outside of the particle sensor.

Meanwhile, the air cleaner can be typically installed in a vertical direction or in a horizontal direction. Such orientation of the installation of the air cleaner may be changed in various manners depending on the individual tastes of users or the installation environment of the air cleaner. Here, the orientation of the particle sensor 10, which is installed in the air cleaner, is also changed depending on the orientation of the air cleaner. In other words, a straight line, which connects the inlet 11, the detection chamber 12 and the outlet 13 to each other, is oriented in the vertical or the horizontal direction depending on the orientation of the air cleaner.

However, in the case where the straight line that connects the inlet 11, the detection chamber 12 and the outlet 13 to each other is oriented in the horizontal direction, air which flows by natural convection cannot smoothly pass through the particle sensor. As a result, the pollution level of air cannot be precisely measured in the detection chamber 12.

Figure 2:
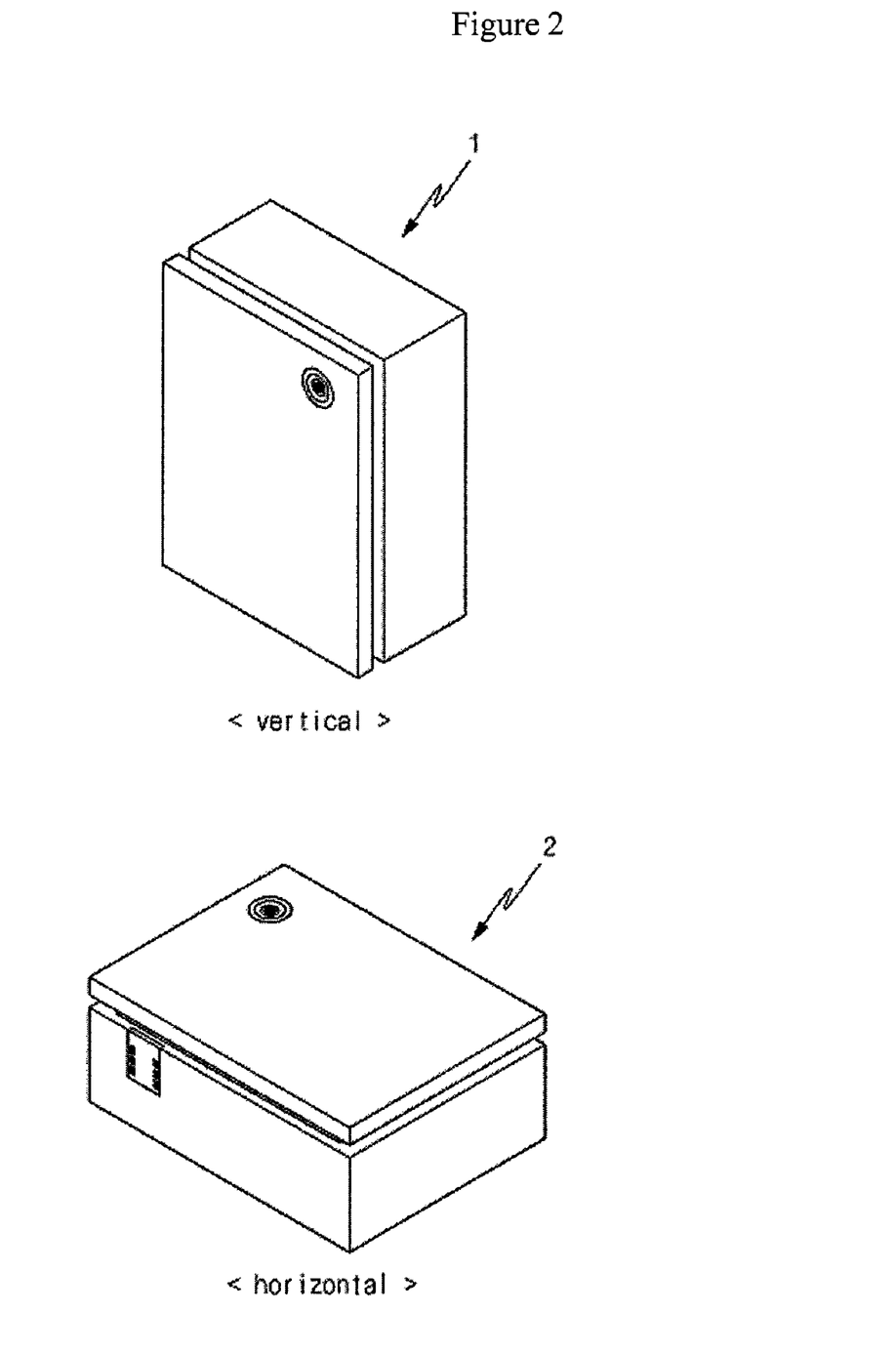
FIG. 2 is of perspective views of air cleaners having the particle sensors of FIG. 1.

That is, referring to FIG. 2, between a vertical (or a stand type) air cleaner 1 and a horizontal (or a table type) air cleaner 2, the orientations of the installed particle sensors 10 differ from each other, as described above.

Therefore, a particle sensor, which is constructed such that an inlet 11, a detection chamber 12 and an outlet 13 can be arranged in the vertical direction regardless of the orientation of an air cleaner, is required.

SUMMARY OF THE INVENTION

Accordingly, the present invention has been made keeping in mind the above problems occurring in the prior art, and an aspect of the present invention provides a rotary particle sensor assembly which is always oriented in a predetermined direction regardless of the orientation of an air cleaner, and the air cleaner having the rotary particle sensor assembly.

In an aspect, the present invention provides a rotary particle sensor assembly, installed in an air cleaner to measure a pollution level of air drawn into the air cleaner, the rotary particle sensor assembly including: a particle sensor to measure the pollution level of the air drawn into the air cleaner, wherein the particle sensor is supported in the air cleaner so as to be rotatable using a rotating shaft and has a weight at a predetermined position thereon, so that the particle sensor is oriented in a direction of gravity by the weight regardless of an orientation of the air cleaner.

In another aspect, the present invention provides a rotary particle sensor assembly, installed in an air cleaner to measure a pollution level of air drawn into the air cleaner, the rotary particle sensor assembly including: a particle sensor to measure the pollution level of the air drawn into the air cleaner; and a particle sensor cover, to which the particle sensor is fastened, with a rotating shaft provided at a predetermined position on an outer surface of the particle sensor cover, the particle sensor cover being mounted in the air cleaner so as to be rotatable, wherein a weight is provided at a predetermined position on the particle sensor or the particle sensor cover, so that the particle sensor cover having the particle sensor is oriented in a direction of gravity by the weight regardless of an orientation of the air cleaner.

The rotary particle sensor assembly may further include a particle sensor cover guide installed at a predetermined position in the air cleaner. The particle sensor cover guide supports the particle sensor or the particle sensor cover therein so as to be rotatable.

Furthermore, a hollow support shaft may protrude from the particle sensor cover guide. The hollow support shaft may be fastened at a predetermined position to an inner surface of the air cleaner. The rotating shaft of the particle sensor or the particle sensor cover may be rotatably inserted into the support shaft.

The particle sensor may have an inlet, into which air is drawn, a detection chamber provided to measure a pollution level of the drawn air, and an outlet, through which the air that is measured in pollution level is discharged outside the particle sensor, wherein the inlet, the detection chamber and the outlet are arranged in a straight line, on which the weight is provided, so that the straight line is oriented in the direction of gravity by the weight.

In addition, a mounting bracket may be provided on the particle sensor cover guide, so that the particle sensor cover guide is fastened to the inner surface of the air cleaner using the mounting bracket.

In another aspect, the present invention provides an air cleaner, having a rotary particle sensor assembly to measure a pollution level of air, the rotary particle sensor assembly, including a particle sensor to measure the pollution level of the air drawn into the air cleaner, wherein the particle sensor is supported in the air cleaner so as to be rotatable using a rotating shaft, a guide protrusion is provided on the particle sensor at a position spaced apart from an inlet of the particle sensor by a predetermined distance, a guide slot is formed in one surface of the air cleaner, having the particle sensor therein, such that the guide protrusion protrudes through the guide slot to an outside of the air cleaner and is movable along the guide slot, and a weight is provided at a predetermined position on the particle sensor, so that the particle sensor assembly is oriented in a direction of gravity by the weight regardless of an orientation of the air cleaner.

In another aspect, the present invention provides an air cleaner, having a rotary particle sensor assembly to measure a pollution level of air, the rotary particle sensor assembly, including: a particle sensor to measure the pollution level of the air drawn into the air cleaner; and a particle sensor cover, to which the particle sensor is fastened, with a rotating shaft provided at a predetermined position on an outer surface of the particle sensor cover, the particle sensor cover being mounted in the air cleaner so as to be rotatable, wherein a guide protrusion is provided on the particle sensor cover at a position spaced apart from an inlet of the particle sensor by a predetermined distance, a guide slot is formed in one surface of the air cleaner, having the particle sensor assembly therein, such that the guide protrusion protrudes through the guide slot to an outside of the air cleaner and is movable along the guide slot, and a weight is provided at a predetermined position on the particle sensor or the particle sensor cover, so that the particle sensor assembly is oriented in a direction of gravity by the weight regardless of an orientation of the air cleaner.

Preferably, the air cleaner may further include a particle sensor cover guide installed at a predetermined position in the air cleaner, the particle sensor cover guide supporting the particle sensor or the particle sensor cover therein so as to be rotatable.

Furthermore, a hollow support shaft may protrude from the particle sensor cover guide, the hollow support shaft being fastened at a predetermined position to an inner surface of the air cleaner, and the rotating shaft of the particle sensor or the particle sensor cover may be rotatably inserted into the support shaft.

The particle sensor may have an inlet, into which air is drawn, a detection chamber to measure a pollution level of the drawn air, and an outlet, through which the air that is measured in pollution level is discharged outside the particle sensor, wherein the inlet, the detection chamber and the outlet are arranged in a straight line, on which the weight is provided, so that the straight line is oriented in the direction of gravity by the weight.

In addition, a mounting bracket may be provided on the particle sensor cover guide, so that the particle sensor cover guide is fastened to the inner surface of the air cleaner using the mounting bracket.

Moreover, an inlet port and an outlet port may be formed through one outer surface of a housing of the air cleaner at respective positions corresponding to the inlet and the outlet of the particle sensor, and the inlet port and the outlet port may comprise a plurality of inlet ports and a plurality of outlet ports corresponding to positions of the inlet and the outlet of the particle sensor which change depending on rotation of the particle sensor.

In a rotary particle sensor assembly and an air cleaner having the rotary particle sensor assembly according to the present invention, a particle sensor is oriented such that an inlet, a detection chamber and an outlet can be arranged in the direction imposed by gravity, that is, in vertically to the ground. Therefore, regardless of the orientation of the air cleaner, the particle sensor can be always oriented in the desired direction, thus ensuring the accuracy of measurement of the pollution level of air.

DETAILED DESCRIPTION

Hereinafter, a rotary particle sensor assembly and an air cleaner having the rotary particle sensor assembly according to a preferred embodiment of the present invention will be described with reference to the attached drawings. In the description of the present invention, reference should now be made to the drawings, in which the same reference numerals are used throughout the different drawings to designate the same or similar components as those of FIGS. 1 and 2, for which further explanation will be skipped.

Figure 3:
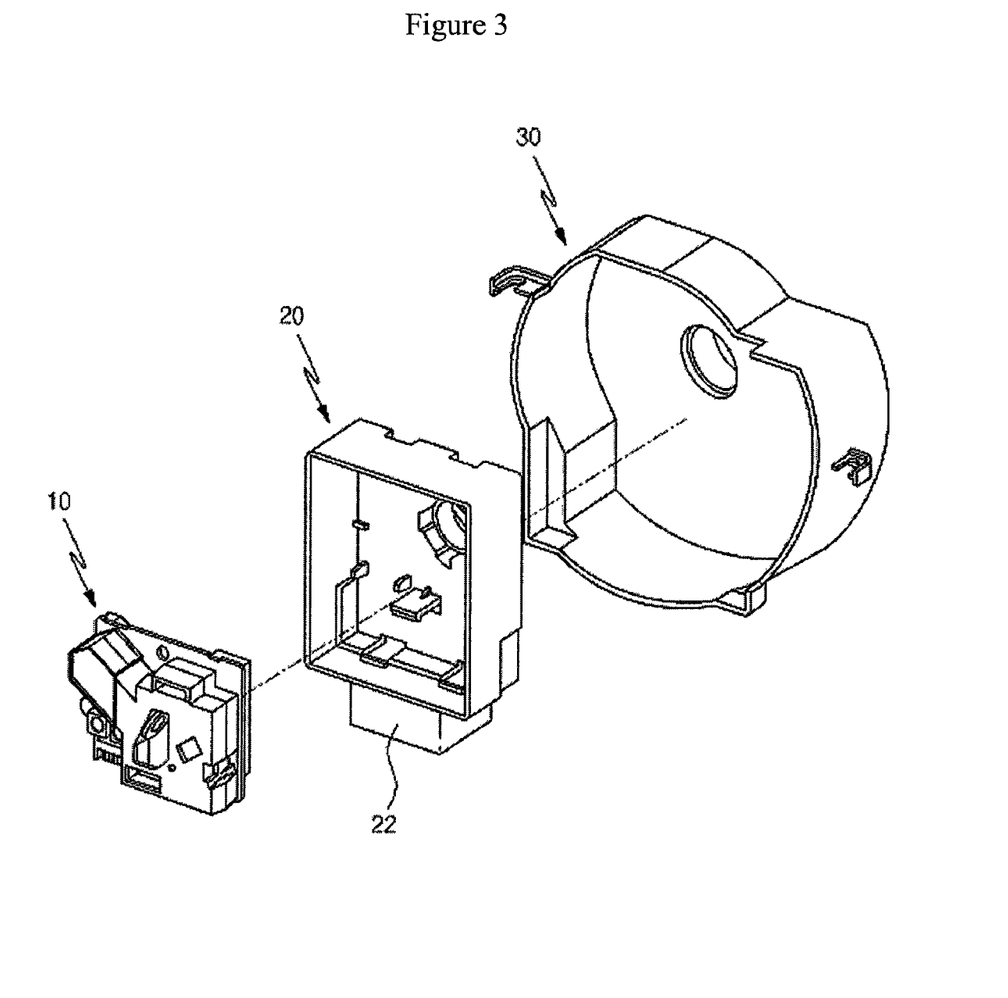
FIG. 3 is an exploded perspective view of a rotary particle sensor assembly, according to an embodiment of the present invention.

Referring to FIG. 3, the rotary particle sensor assembly according to the preferred embodiment of the present invention includes a particle sensor 10, which measures a pollution level of air drawn into the air cleaner, a particle sensor cover 20, which supports the particle sensor therein and has a weight 22 on one surface thereof, and a particle sensor cover guide 30, which is fastened to the inner surface of the air cleaner. The particle sensor cover 20 is rotatably mounted to the particle sensor cover guide 30.

Here, the rotary particle sensor assembly may mean only the particle sensor 10 or the coupling between the particle sensor 10 to the particle sensor cover 20. In other words, the rotary particle sensor assembly may comprise only the particle sensor 10. Alternatively, the rotary particle sensor assembly may comprise the particle sensor 10 and the particle sensor cover 20, which are coupled to each other. In the case where the rotary particle sensor assembly comprises only the particle sensor 10, it may be mounted in the air cleaner using a rotating shaft.

Of course, in the present invention, the particle sensor cover guide 30 may be optionally used. Furthermore, the weight 22 may be provided at a predetermined position on the particle sensor 10.

The particle sensor 10 has the same structure as that of the particle sensor 10 of FIG. 1. As depicted in FIG. 1, the particle sensor 10 of the present invention has an inlet 11, into which air is drawn, a detection chamber 12, which is provided to measure a pollution level of the drawn air, and an outlet 13, through which the air that is measured in pollution level is discharged to the outside of the particle sensor 10.

Preferably, as shown in FIG. 3, the inlet 11, the detection chamber 12 and the outlet 13 are arranged in a straight line, on which the weight 22 is provided, so that the straight line can always be oriented in the direction of gravity by the weight 22. Here, it is to be understood that the term "the orientation of the straight line in the direction of gravity" means that the straight line is perpendicular to the ground such that it is aligned with the direction imposed by gravity.

The particle sensor cover 20 serves to support the particle sensor 10 therein. The weight 22 is mounted to one surface of the particle sensor cover 20. The particle sensor cover 20 firmly supports the particle sensor 10 such that the particle sensor 10 can maintain the fixed position relative to the particle sensor cover 20. Therefore, when the particle sensor cover 20 is rotated, the particle sensor 10 is also rotated along with the particle sensor cover 20.

The particle sensor cover 20, which supports the particle sensor 10 therein, is rotatably mounted to the particle sensor cover guide 30. The particle sensor cover guide 30 is installed in the air cleaner.

Figure 4:
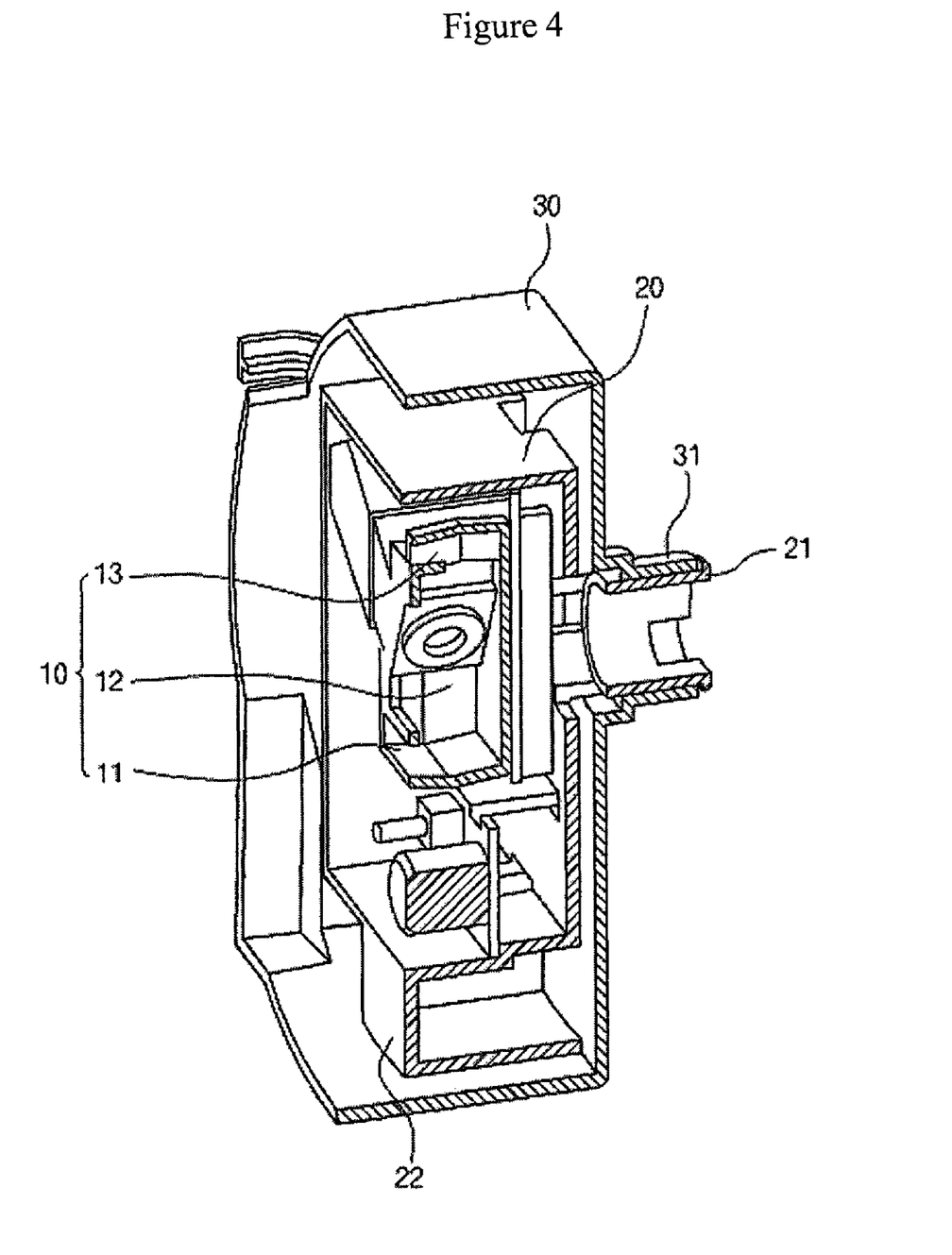
FIG. 4 is a sectional perspective view of the assembled particle sensor assembly of FIG. 3.

The coupling between the particle sensor 10, the particle sensor cover 20 and the particle sensor cover guide 30 will be explained below in detail with reference to FIG. 4.

As described above, the particle sensor 10 is fastened to the particle sensor cover 20 and thus maintains a fixed position relative to the particle sensor cover 20. However, a method of fastening the particle sensor to the particle sensor cover is not limited to a special coupling method. For example, a bracket (not shown) is provided on the outer surface of the particle sensor 10, and a coupling boss (not shown) is provided in the particle sensor cover 20, so that the particle sensor 10 is fastened to the particle sensor cover 20 by coupling the bracket to the coupling boss using a typical screw.

The particle sensor cover 20, to which the particle sensor 10 is fastened, is rotatably mounted to the particle sensor cover guide 30. The particle sensor cover guide 30 is installed at the stationary position in the air cleaner, as stated above. To rotatably mount the particle sensor cover 20 to the particle sensor cover guide 30, a rotating shaft 21 protrudes from one surface of the particle sensor cover 20. The rotating shaft 21 is rotatably inserted into a support shaft 31, which is provided in the particle sensor cover guide 30.

Because the rotating shaft 21 is rotatable relative to the support shaft 31, it is preferable that the outer diameter of the rotating shaft 21 be slightly shorter than the inner diameter of the support shaft 31.

With regard to the installation position of the rotating shaft 21, in the case where the rotating shaft 21 is designed such that it is aligned with the detection chamber 12 of the particle sensor 10, the size of the particle sensor 10 can be minimized, and a discharge hole of the air cleaner, which communicates with the inlet 11 for inflow of air and with the outlet 13 for discharge of air, can be minimized. Therefore, it is preferable that the rotating shaft 21 is designed on the basis of the detection chamber 12 of the particle sensor 10 such that it is aligned with the detection chamber 12.

Furthermore, mounting brackets 32 are provided on the outer surface of the particle sensor cover guide 30. Thus, the particle sensor assembly is firmly coupled to the air cleaner using the mounting brackets 32. Here, a method of coupling the particle sensor assembly to the air cleaner is not limited to a special method. Typically, the particle sensor assembly can be coupled to the air cleaner by fastening the mounting brackets 32 to the surface of the air cleaner using screws.

Hereinafter, the operation of the rotary particle sensor assembly according to the embodiment of the present invention will be explained in detail with reference to FIG. 5.

Figure 5:
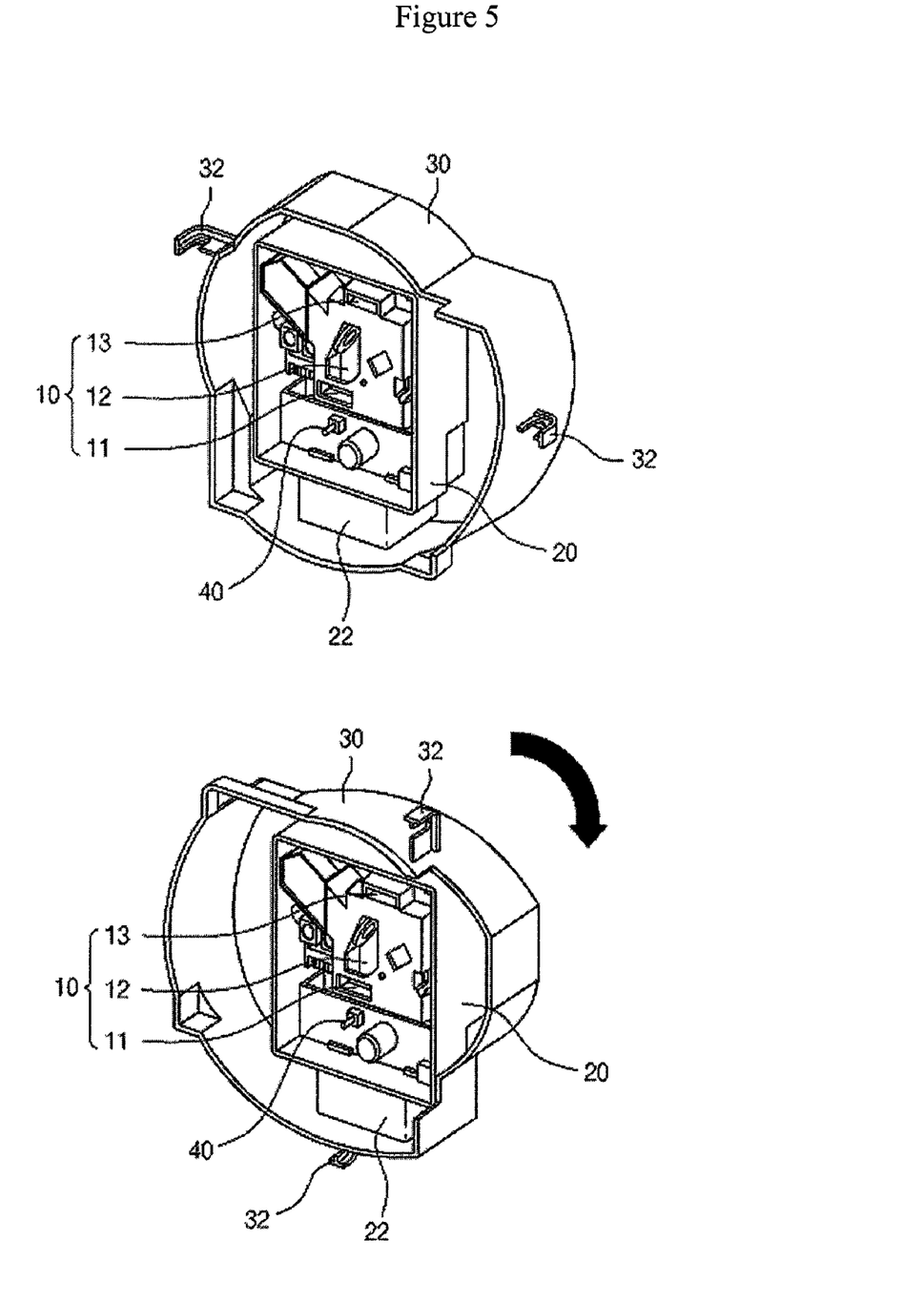
FIG. 5 is of views showing the operating principle of the particle sensor assembly of FIG. 3.

The upper view of FIG. 5 illustrates the rotary particle sensor assembly installed in the vertical air cleaner 1 (see, FIG. 2). The lower view of FIG. 5 illustrates the rotary particle sensor assembly installed in the horizontal air cleaner 2 (see, FIG. 2).

Here, the terms "vertical air cleaner 1" and "horizontal air cleaner 2" do not mean two separate air cleaners. Because one air cleaner can be selectively installed in the vertical direction or the horizontal direction, it can be appreciated that the terms are used only for descriptive purpose.

In the case of the particle sensor 10 according to the conventional technique, if the air cleaner, which must be illustrated in the vertical direction, is oriented in the horizontal direction (and vice-versa), the straight line, which connects the inlet 11, the detection chamber 12 and the outlet 13 to each other and is parallel to the vertical line relative to the ground, is oriented in the horizontal direction. In this case, inflow and discharge of air, which flows by natural convection, become uneven, with the result that the pollution level of air cannot be precisely measured. This has been already illustrated above.

However, the rotary particle sensor assembly according to the present invention is rotatably mounted to the particle sensor cover guide 30, and the weight 22 is provided on the surface of the particle sensor cover 20, which has the particle sensor 10 therein. Accordingly, the weight 22 can always be oriented in the direction imposed by gravity, regardless of the orientation of the air cleaner.

Therefore, even if the orientation of the air cleaner is changed from the vertically installed state to the horizontally installed state or from the horizontally installed state to the vertically installed state, or even if it is changed into the state of being installed at various angles, the particle sensor cover 20 can be always oriented in the direction of gravity, that is, in the vertical direction, by the weight 22.

Here, the inlet 11, the detection chamber 12 and the outlet 13 are constructed such that they are arranged in the straight line, on which the weight 22 is disposed. Hence, the inlet 11, the detection chamber 12 and the outlet 13 are arranged on the straight line parallel to the direction of gravity.

Air, which is drawn into the air cleaner by natural convection, is moved upwards from the lower portion of the air cleaner to the upper portion thereof by differing densities of air. At this time, because the inlet 11, the detection chamber 12 and the outlet 13 are always in the straight line parallel to the direction of gravity, the pollution level of air can be precisely measured regardless of the orientation of the air cleaner.

In detail, air drawn into the inlet 11 is expanded by heat generated from a resistor, a typical electronic component provided around the inlet 11, and thus the air is reduced in density. Therefore, air is moved upwards in the direction opposite gravity and then passes through the detection chamber 12. Thereafter, the air is discharged to the outside of the air cleaner through the outlet 13. At this time, the detection chamber 12 can precisely measure a pollution level of air, because the straight line, connecting the inlet 11, the detection chamber 12 and the outlet 13 to each other, is always oriented in the direction of gravity regardless of the orientation of the air cleaner.

Below, the construction and principle of the air cleaner having the particle sensor assembly according to the embodiment of the present invention will be explained with reference to FIGS. 5 and 6.

Referring to FIG. 5, a guide protrusion 40 is provided on the particle sensor cover 20. The guide protrusion 40 is inserted into a guide slot 118, which is formed in a housing 100 of the air cleaner, thus guiding the rotation of the particle sensor cover 20.

Figure 6:
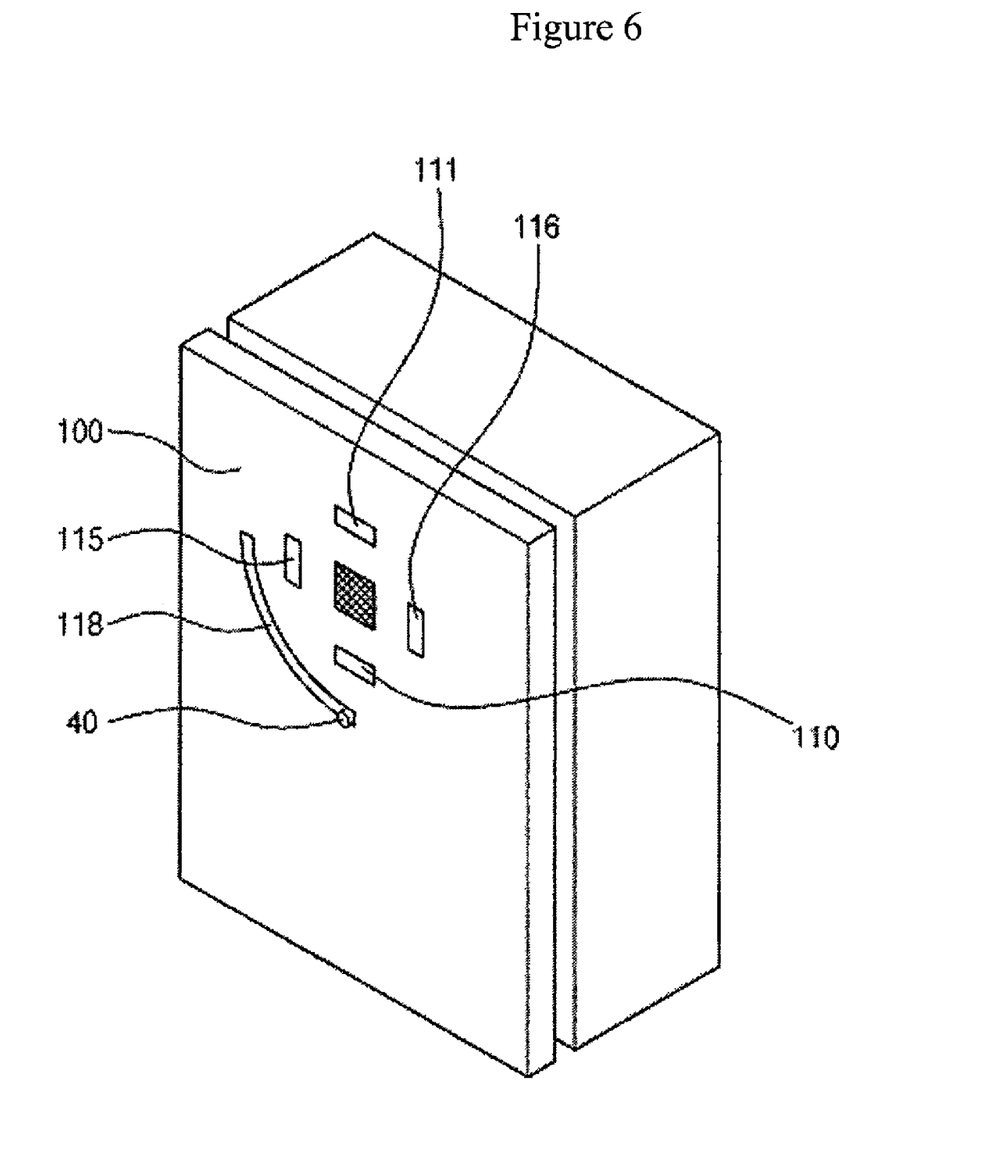
FIG. 6 is a perspective view of an air cleaner having the particle sensor assembly of FIG. 3.

As shown in FIG. 6, a first inlet port 110 and a second inlet port 115, which correspond to the inlet 11 of the particle sensor 10, and a first outlet port 111 and a second outlet port 116, which corresponding to the outlet 13 of the particle sensor 10, are formed in the housing 100 of the air cleaner.

The support shaft 31 of the particle sensor cover guide 30 is rotatably coupled to a bracket (not shown), which is provided on the inner surface of the air cleaner. The particle sensor cover 20 and the particle sensor 10 are rotatable around the support shaft 31, as stated above.

Here, with the passage of time, the rotation of the particle sensor 10 around the support shaft 31 may become uneven due to friction or uneven abrasion.

In this case, a user can manually rotate the particle sensor 10 using the guide protrusion 40, which is exposed to the outside of the housing 100 of the air cleaner.

At this time, the guide protrusion 40 is moved along the guide slot 118, which is curved and is formed in the housing 100 of the air cleaner.

Therefore, the inlet, the detection chamber and the outlet of the particle sensor can always be arranged in the vertical direction, that is, in the direction of imposed by gravity. Thus, the present invention has an advantage in that, regardless of the orientation of the air cleaner, the particle sensor can precisely measure the pollution level of air.

Although the preferred embodiment of the present invention has been disclosed for illustrative purposes, the present invention is not limited to the particular embodiment described above. In other words, those skilled in the art will appreciate that various modifications, additions and substitutions are possible, without departing from the scope and spirit of the present invention as disclosed in the accompanying claims. Furthermore, these modifications, additions and substitutions must be regarded as falling within the bounds of the present invention.

The invention claimed is:

1. A rotary particle sensor assembly, installed in an air cleaner to measure a pollution level of air drawn into the air cleaner, the rotary particle sensor assembly comprising:
   a particle sensor to measure the pollution level of the air drawn into the air cleaner, wherein the particle sensor is supported in the air cleaner so as to be rotatable using a rotating shaft and has a weight at a predetermined position thereon, so that the particle sensor is oriented in a direction of gravity by the weight regardless of an orientation of the air cleaner.

2. A rotary particle sensor assembly, installed in an air cleaner to measure a pollution level of air drawn into the air cleaner, the rotary particle sensor assembly comprising:
   a particle sensor to measure the pollution level of the air drawn into the air cleaner; and
   a particle sensor cover, to which the particle sensor is fastened, with a rotating shaft provided at a predetermined position on an outer surface of the particle sensor cover, the particle sensor cover being mounted in the air cleaner so as to be rotatable, wherein
   a weight is provided at a predetermined position on the particle sensor or the particle sensor cover, so that the particle sensor cover having the particle sensor is oriented in a direction of gravity by the weight regardless of an orientation of the air cleaner.

3. The rotary particle sensor assembly according to claim 1 or 2, further comprising:
   a particle sensor cover guide installed at a predetermined position in the air cleaner, the particle sensor cover guide supporting the particle sensor or the particle sensor cover therein so as to be rotatable.

4. The rotary particle sensor assembly according to claim 3, wherein a hollow support shaft protrudes from the particle sensor cover guide, the hollow support shaft being fastened at a predetermined position to an inner surface of the air cleaner, and
   the rotating shaft of the particle sensor or the particle sensor cover is rotatably inserted into the support shaft.

5. The rotary particle sensor assembly according to claim 1 or 2, wherein the particle sensor has an inlet, into which air is drawn, a detection chamber provided to measure a pollution level of the drawn air, and an outlet, through which the air that is measured in pollution level is discharged outside the particle sensor, wherein
   the inlet, the detection chamber and the outlet are arranged in a straight line, on which the weight is provided, so that the straight line is oriented in the direction of gravity by the weight.

6. The rotary particle sensor assembly according to claim 4, wherein a mounting bracket is provided on the particle sensor cover guide, so that the particle sensor cover guide is fastened to the inner surface of the air cleaner using the mounting bracket.

7. An air cleaner, having a rotary particle sensor assembly to measure a pollution level of air,
   the rotary particle sensor assembly, comprising a particle sensor to measure the pollution level of the air drawn into the air cleaner, wherein
   the particle sensor is supported in the air cleaner so as to be rotatable using a rotating shaft,
   a guide protrusion is provided on the particle sensor at a position spaced apart from an inlet of the particle sensor by a predetermined distance,
   a guide slot is formed in one surface of the air cleaner, having the particle sensor therein, such that the guide protrusion protrudes through the guide slot to an outside of the air cleaner and is movable along the guide slot, and
   a weight is provided at a predetermined position on the particle sensor, so that the particle sensor assembly is oriented in a direction of gravity by the weight regardless of an orientation of the air cleaner.

8. An air cleaner, having a rotary particle sensor assembly to measure a pollution level of air,
   the rotary particle sensor assembly, comprising: a particle sensor to measure the pollution level of the air drawn into the air cleaner; and
   a particle sensor cover, to which the particle sensor is fastened, with a rotating shaft provided at a predetermined position on an outer surface of the particle sensor cover, the particle sensor cover being mounted in the air cleaner so as to be rotatable, wherein
   a guide protrusion is provided on the particle sensor cover at a position spaced apart from an inlet of the particle sensor by a predetermined distance,
   a guide slot is formed in one surface of the air cleaner, having the particle sensor assembly therein, such that the guide protrusion protrudes through the guide slot to an outside of the air cleaner and is movable along the guide slot, and a weight is provided at a predetermined position on the particle sensor or the particle sensor cover, so that the particle sensor assembly is oriented in a direction of gravity by the weight regardless of an orientation of the air cleaner.

9. The air cleaner having the rotary particle sensor assembly according to claim 7 or 8, further comprising:

a particle sensor cover guide installed at a predetermined position in the air cleaner, the particle sensor cover guide supporting the particle sensor or the particle sensor cover therein so as to be rotatable.

10. The air cleaner having the rotary particle sensor assembly according to claim 9, wherein a hollow support shaft protrudes from the particle sensor cover guide, the hollow support shaft being fastened at a predetermined position to an inner surface of the air cleaner, and the rotating shaft of the particle sensor or the particle sensor cover is rotatably inserted into the support shaft.

11. The air cleaner having the rotary particle sensor assembly according to claim 7 or 8, wherein the particle sensor has an inlet, into which air is drawn, a detection chamber to measure a pollution level of the drawn air, and an outlet, through which the air that is measured in pollution level is discharged outside the particle sensor, wherein the inlet, the detection chamber and the outlet are arranged in a straight line, on which the weight is provided, so that the straight line is oriented in the direction of gravity by the weight.

12. The air cleaner having the rotary particle sensor assembly according to claim 10, wherein a mounting bracket is provided on the particle sensor cover guide, so that the particle sensor cover guide is fastened to the inner surface of the air cleaner using the mounting bracket.

13. The air cleaner having the rotary particle sensor assembly according to claim 7 or 8, wherein an inlet port and an outlet port are formed through one outer surface of a housing of the air cleaner at respective positions corresponding to the inlet and the outlet of the particle sensor, and the inlet port and the outlet port comprise a plurality of inlet ports and a plurality of outlet ports corresponding to positions of the inlet and the outlet of the particle sensor which change depending on rotation of the particle sensor.

* * * * *

UNITED STATES PATENT AND TRADEMARK OFFICE
CERTIFICATE OF CORRECTION

PATENT NO. : 8,365,578 B2
APPLICATION NO. : 12/672541
DATED : February 5, 2013
INVENTOR(S) : Jun Hyung Bae Page 1 of 1

It is certified that error appears in the above-identified patent and that said Letters Patent is hereby corrected as shown below:

On the Title Page:

Item (30), Foreign Application Priority Data, add -- KR 10-2008-0077147   08/06/2008 --

Signed and Sealed this
Seventh Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO.         : 8,365,578 B2                                                    Page 1 of 1
APPLICATION NO.    : 12/672541
DATED              : February 5, 2013
INVENTOR(S)        : Jun Hyung Bae It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 560 days.

Signed and Sealed this

First Day of September, 2015

Michelle K. Lee
*Director of the United States Patent and Trademark Office*